United States Patent [19]

Salmasian

[11] Patent Number: 4,592,342
[45] Date of Patent: Jun. 3, 1986

[54] METHOD FOR APPETITE SUPPRESSION AND WEIGHT LOSS MAINTENANCE AND DEVICE

[76] Inventor: Samuel S. Salmasian, 2034 Hidden Crest Dr., El Cajon, Calif. 92020

[21] Appl. No.: 567,669

[22] Filed: Jan. 3, 1984

Related U.S. Application Data

[63] Continuation-in-part of Ser. No. 490,317, May 2, 1983, abandoned.

[51] Int. Cl.⁴ ............................................. A61B 19/00
[52] U.S. Cl. ....................................... 128/1 R; 128/96; 128/118; 128/133
[58] Field of Search .......................... 128/1 R, 95–101, 128/118, 133, 134

[56] References Cited

U.S. PATENT DOCUMENTS

| 2,240,308 | 4/1941 | Mahe | 128/96 |
| 2,493,406 | 1/1950 | Hicks | 128/96 |
| 2,671,899 | 3/1954 | Kroger | 128/96 X |
| 3,145,710 | 8/1964 | Schott | 128/100 |
| 3,467,085 | 9/1969 | Cormier | 128/134 X |
| 3,578,773 | 5/1971 | Schultz | 128/96 X |
| 4,204,534 | 5/1980 | Leary | 128/134 |

FOREIGN PATENT DOCUMENTS 383907 1/1908 France ................................. 128/96

Primary Examiner—Dalton L. Truluck
Attorney, Agent, or Firm—Lyon & Lyon

[57] ABSTRACT

A special belt is provided for effecting weight loss in the wearer. A central body has a convex side which is pressed into the abdomen about three fingers over the navel. The constant pressure both decreases the appetite and the ability of the stomach to hold large amounts of food.

30 Claims, 24 Drawing Figures

U.S. Patent   Jun. 3, 1986   Sheet 1 of 3   4,592,342
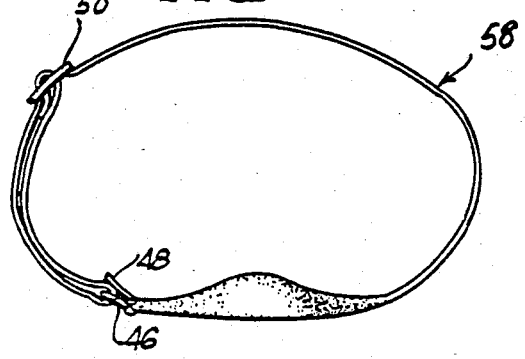
FIG. 1
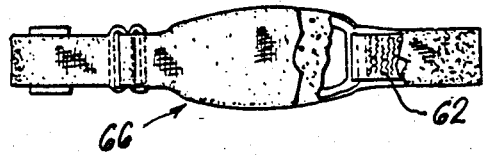
FIG. 2
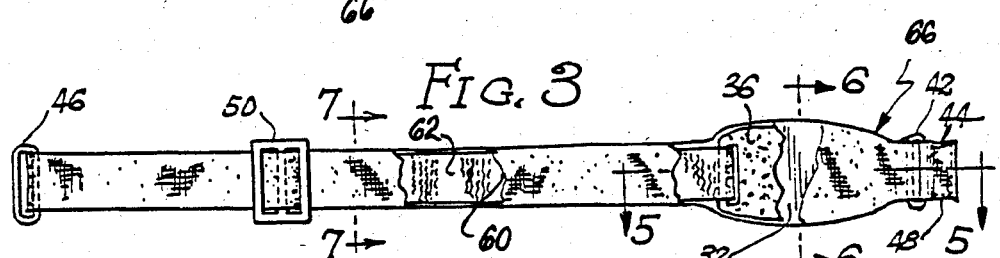
FIG. 3
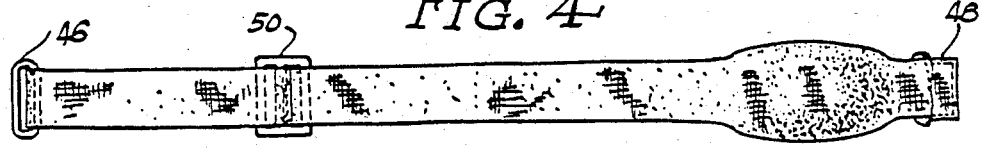
FIG. 4
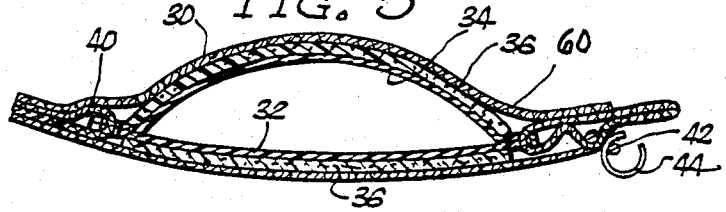
FIG. 5
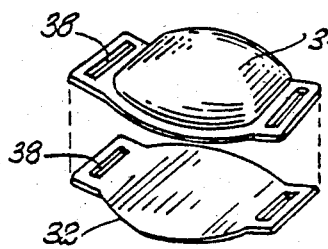
FIG. 8
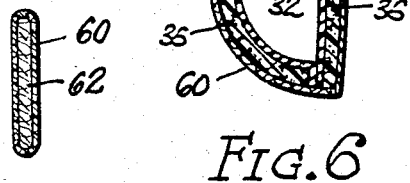
FIG. 7
FIG. 6

METHOD FOR APPETITE SUPPRESSION AND WEIGHT LOSS MAINTENANCE AND DEVICE

BACKGROUND OF THE INVENTION

The instant invention is a continuation-in-part of an invention entitled MEANS AND METHOD OF EFFECTING WEIGHT LOSS BY CONTROLLING THE APPETITE filed May 2, 1983 having Ser. No. 06/490,317, which is incorporated herein by reference and which has been abandoned. The current invention comprises improvements and modifications of the original weight reduction belt.

The original device described in the above cited patent application operated on the same principles as do the improvements and modifications described and claimed herein. The principle upon which all the devices operate is that of displacing the abdomen inwardly from the front by means of an object which is cinched fairly tightly around the body. the object should be located with its lower edge about three fingers above the navel. When it is in this position, and the appropriate pressure applied, there is the feeling of having something in one's stomach which tends to reduce the appetite. Also, by physically displacing into much of the stomach's volume, less food can be consumed at any one time. If the pressure is great enough, it may evan become difficult to swallow if the stomach is partially full.

The initial invention set forth in the parent application was used experimentally, and was used as a basis for developing a more refined product. It consisted of a vacuum-formed sheet of plastic having one distended side which was simply strapped to the body using a Velcro adjustable strap. It was a little rough around the edges, although it proved very effective in testing and experimentation.

By testing the original unit plus its improved progeny, the effectiveness of the technique has been proven beyond a doubt. Several dozen people, primarily women, have been and are wearing the belt with striking, and exciting results. Over a period of about seven weeks, it is not uncommon for a typical patient to lose twenty pounds, and even more. To date, no side effects have become apparent. As it became clear that this very simple approach to weight reduction may actually be revolutionary in the weight reduction business, and dramatically improve the lives of millions of people suffering from overweight and obesity, the need for additional patent protection, covering the improvements of the original model, became apparent.

SUMMARY OF THE INVENTION

The instant invention utilizes the same basic principles used in the original model, but has been substantially improved, both in ease of use, and in comfort to the wearer. The central body is now covered on both sides with a layer of soft foam for the comfort of the wearer. The original belt with the Velcro ends has been replaced with a belt having a tension adjustment buckle, and the the belt itself is made from an elastic band covered with a sheath of stretchable cloth. Thus, the belt adjusts as the person sits down, stands up and otherwise effectively changes his or her girth, and is much more comfortable. Because the cloth sheath which covers the elastic belt expands to smoothly cover the enlarged body which presses against the abdomen, the exterior of the belt now has a smooth, finished appearance. The units in production have a pink, satin look which has no prosthetic or medical appearance, but almost looks cosmetic in nature.

In addition to the elastic belt and the foam padding, with the improved adjustability, a number of different variations have been conceived. Different shapes of the central protrusion have been developed, and it has been found that the hollow nature of the central body provides a resonating capability which is effective in soothing the stomach when it is tapped several times by the wearer when he or she may become hungry. Division of this resonant chamber into more than one cavity to produce a different resonant effect is disclosed, together with a solid central body, and a liquid filled central body.

BRIEF DESCRIPTION OF THE DRAWINGS

FIG. 1 is a top plan view of the invention;

FIG. 2 is an elevation view of the belt as seen from the bottom of the belt of FIG. 1;

FIG. 3 is the elevation of FIG. 2, but with the belt extended rather than being buckled;

FIG. 4 is an elevational view taken from the opposite direction as FIG. 3;

FIG. 5 is a section taken along 5—5 of FIG. 3;

FIG. 6 is a sectional view taken along lines 6—6 of FIG. 3;

FIG. 7 is a sectional view taken along lines 7—7 of FIG. 3;

FIG. 8 illustrates the body portion exploded into its two component parts;

DETAILED DESCRIPTION OF THE PREFERRED EMBODIMENTS

Figure 9:
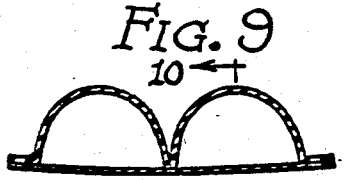
FIG. 9 illustrates an alternative embodiment using two lobes.
Figure 11:
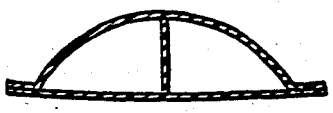
FIG. 11 illustrates the body portion split into two resonant cavities.

FIG. 1 illustrates the overall appearance of the belt from the top. The belt itself indicated at 24 is comprised of a continuous outer sheath 26 which covers elastic band 28 as well as the central body 30. The cloth sheath is continuous over the joints between the elastic in the central body as can be seen in FIG. 1, to produce a very finished appearance in the product.

The body itself, although subject to considerable variation, in the preferred embodiment comprises a pair of vacuum-formed parts 32 and 34. The first part, part 32, has a slight, smooth contour as can best be seen in FIG. 5. This is the externally worn part, and the contour is such that when worn under the clothing, no bulge is apparent to anyone. In use, the belt presses into the flesh of the user so that it is substantially flush and not visible from outside.

The second part 34 defines the bulge which is effective in causing the weight loss. Both parts are bonded together as best seen in FIG. 5, and covered with a layer of foam 36. The elastic band 28 passes through a series of slots 38 in both plastic parts. As shown in FIG. 5, the left end then terminates with the stitched loop 40, whereas the right side engages square metal D-ring 42, which mounts the semi-cylindrical hook 44. The hook engages then a second D-ring 46 at the other end of the belt. A short flap of cloth 48 protects the wearer from the hook buckle point. Along the length of the belt is a standard buckle adjustment 50 which controls the size of the belt, and therefore the pressure that is applied to the abdomen. This permits the buckle to be set semi-permanently to the tension that is optimal, with the belt being removable at the hook so that the tension does not require resetting every time the belt is removed.

This construction makes the belt smooth, visually attractive, comfortable to wear, and unobtrusive. It is both unobtrusive physically and visually. Once the wearer has been using the belt for a few hours, he or she no longer notices that it is on. In fact, many patients get so accustomed to the belt that they feel uncomfortable when it is off. The belt yields to many patients a warm, comfortable feeling as though they had just eaten a nice meal. Provided that the clothing worn by the patient is completely opaque, the belt is not visible by means of any protuberances or distortions of the body to anyone. It is soft, comfortable, and attractive. To mount the belt, first the body is positioned with the lower edge three fingers above the navel, and engaged by tensioning the belt. Then, the belt is increasingly tensioned until the wearer experiences discomfort, at which point the tension is abated until the discomfort abates. This is the optimal tension.

Figure 10:
FIG. 10 is a section taken along line 10—10 of FIG. 9.
Figure 12:
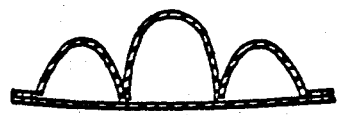
FIG. 12 illustrates a three mounds embodiment of the main body.
Figure 13:
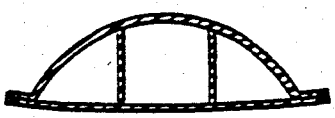

A number of different embodiments have been illustrated in FIGS. 9-21, showing different approaches to the formation of the body and similar variations. FIGS. 9-13 illustrate different ways of providing the body as several different resonant chambers rather than one. In FIGS. 9, 10, and 12, this is done by sculpting separate chambers, and in FIGS. 11 and 13, internal baffles define the different cavities. The resonance is helpful in transmitting an appetite supressing vibration to the stomach. In another embodiment, any of the hollow versions of the body could be partially filled with water to stimulate the stomach with temperature difference and/or the vibrating sloshing action of the water.

Figure 14:
FIGS. 14–16 illustrate verious shapes the main body could assume.
Figure 15:
Figure 16:
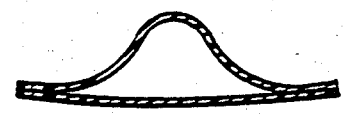
Figure 17:
FIG. 17 illustrates a modification which has an expandable portion and a valved bulb pump.
Figure 18:
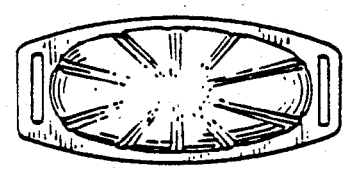
FIG. 18 is a top plan view of the embodiment shown in FIG. 16.
Figure 19:
FIG. 19 is an embodiment utilizing a surface textured with ovate ribs.
Figure 20:
FIG. 20 illustrates the surface of the body textured with parallel ribs.
Figure 21:
FIG. 21 illustrates a sectional view of a solid foam with an optional rigid backing body; and, FIG. 22 is a perspective view of a single warped plane plastic embodiment.

FIGS. 14 and 15 illustrate main bodies which have been contoured by the provision of parallel ridges in FIG. 14 and spaced protrusions in FIG. 15. FIG. 16 is partially convex along its base area to provide a more accented point. FIG. 17 illustrates a means of inflating an inflatable version of the body, similar to the inflatable version illustrated in the parent application but using a valved squeeze bulb for pressure rather than a carbon dioxide cartridge. FIG. 18 illustrates how the FIG. 16 embodiment might look if it were star-shaped, and FIG. 19 illustrates a body contoured with concentric ovate ribs. FIG. 20 carries the same concept from FIG. 19 into parallel ribs, similar to FIG. 14. FIG. 21 illustrates a body composed of a solid mass of material 54 such as medium-density, semi-flexible XYLOFOAM foam, with a rigid backing 56. The backing is optionsl and could be omitted provided the foam were strong enough to support the belt.

Figure 22:
Figure 23:
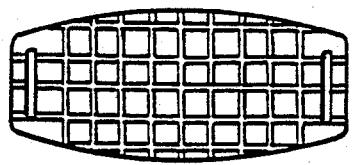
FIG. 23 is an embodiment illustrating a striation grid on the face of the body.
Figure 24:
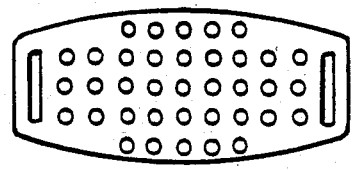
FIG. 24 illustrates a perforated version of the body.
Figure 25:
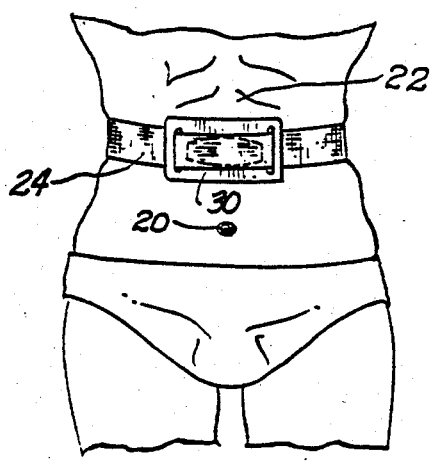
Figure 26:
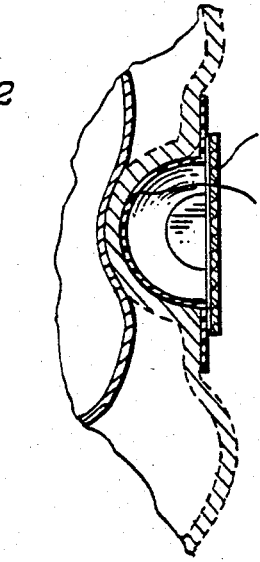
Figure 27:
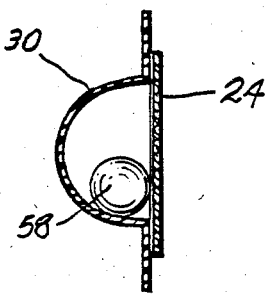
Figure 28:
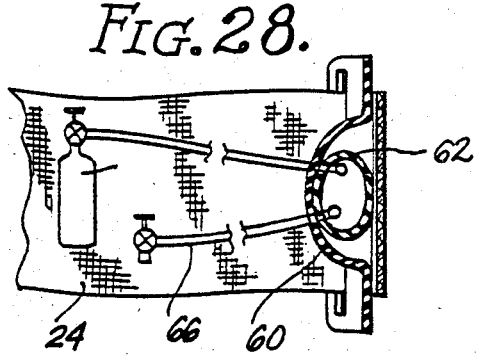
Figure 29:
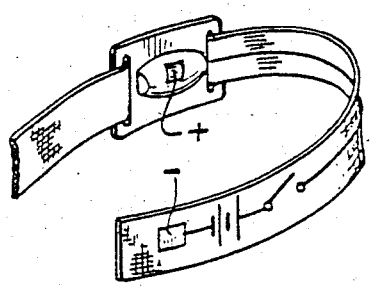

The embodiment shown in FIG. 22 is a single molded piece of plastic with slotted ends to engage the belt. This piec is a warped plane with no curve in the vertical dimension, like a ribbon or belt. Ordinarily it would be coated with a foam material such as the preferred embodiment, but of course this would not be necessary to effectuate the results desired. FIG. 23 illustrates an embodiment having a striated, texturized surface, which might be useful, for example, if one wore a silk undergarment under the body which would cause it to otherwise slip were it not texturized. FIG. 24 illustrtes a body that is perforated, to allow it to breathe in case the person had a perspiration problem. In any of the hollow embodiments, the hollow body could be all or partially filled with water or another liquid, for purposes of providing mass or heat conductivity, and in the case of a partially filled body, provide for a certain amount of sloshing around to stimulate the stomach.

It is intended that the claims in this application cover any modification of contour or shape of the central body, provided it serves the one function for which it is designed, to press into the abdomen. Similarly, the belt arrangement has the primary function of pressing the central body into the abdomen, and any other means of compressing the abdomen using an object similar to the main body of the instant invention is intended to be covered by the appended claims.

It is believed that this invention and that disclosed in the parent application provide a significant breakthrough in the area of weight loss, and will assist at least some of the millions of people suffering not only the detrimental health aspects of being obese, but even more so the negative self image that obesity creates and the difficulties that come with it.

What is claimed is:

1. An appetite suppression device which permits extended wear and is effective in causing weight loss comprising a body having a three-dimensional protuberance having an inwardly extending convex surface and an opposing outer surface which has a lesser degree of convexity and belt means for mounting said protuberance on a human being so as to exert pressure inwardly against a portion of the abdomen of the human being, said means being adapted to mount said protuberance between the navel and the sternum and approximately three fingers above the navel of the human being.

2. The device of claim 1 wherein said protuberance is covered with a material capable of absorbing moisture and wherein said belt is removably attached by a fastening means to one end of said protuberance and wherein said belt is adjustable to the size of the wearer.

3. The device of claim 1 wherein said outer surface of said body is smooth.

4. The device of claim 1 wherein said body has more than one inwardly extending protuberances.

5. Structure according to claim 1 wherein said belt comprises an elastic band is covered with a continuous cloth sheath.

6. Structure according to claim 3 wherein said cloth sheath is stretchable.

7. Structure according to claim 4 wherein said belt is infinitely adjustably tensionable to apply the optimum pressure to the abdomen.

8. Structure according to claim 1 wherein said body comprises a single, at least semi-rigid, band contoured in the horizontal dimension to protrude into the abdomen, and at least partially contoured in the vertical dimension in the same sense as in the horizontal.

9. Structure according to claim 1 wherein said three-dimensional body comprises an inner core member covered with soft foam.

10. Structure according to claim 1 wherein said core member is hollow and fabricated of plastic.

11. Structure according to claim 10 wherein said inner core member comprises two mated parts, the first part being gradually curved to substantially conform to the unaltered contour of the abdomen, and the second part being distended away from the first part to protrude into the abdominal area.

12. Structure according to claim 11 wherein at least one of said two parts has ends defining slots and said means of releasibly compressing comprises belt engaged in said slots.

13. Structure according to claim 1 wherein said protuberance takes the form of a plurality of ribs.

14. Structure according to claim 1 wherein said protuberance takes the form of a plurality of mounds.

15. Structure according to claim 1 wherein said body is hollow and substantially sealed to define a resonant chamber.

16. Structure according to claim 15 wherein said resonant chamber is subdivided by internal baffles into a plurality of separate compartments.

17. Structure according to claim 1 wherein said body has one side away from the abdomen and a second side for pressing into the abdomen, and said second side is convex at its central area with a concave shoulder surrounding the central area.

18. Structure according to claim 1 wherein said body is solid.

19. Structure according to claim 18 wherein said solid body is solid plastic foam.

20. Structure according to claim 19 wherein said solid plastic foam is backed by a rigid panel.

21. Structure according to claim 1 wherein said body is hollow and at least partially filled with liquid.

22. Structure according to claim 1 wherein said body is hollow and sealed, and at least a portion of said body which compresses against the abdomen is expansible, and including a tube and valved squeeze-bulb for pressurizing or depressurizing said body.

23. Structure according to claim 1 wherein said body has a surface which protrudes into the abdomen and which is striated.

24. Structure according to claim 1 wherein said body has a surface which protrudes into the abdomen which is perforated.

25. Structure according to claim 1 wherein said body comprises a single warped plane band-shaped member with a central protrusion for protruding into the abdomen.

26. The method of suppressing appetite in human beings for the purpose of achieving effective weight loss comprising removably mounting on a human being a device comprising a means including an inwardly extending protuberance and a belt means for holding said protuberance in a position between the sternum and the navel and approximately three fingers above the navel of the wearer where it can be worn comfortably for extended periods of time and will effectively suppress the appetite of the wearer and wearing said device for an extended period of time sufficient for effecting weight loss.

27. The method of claim 26 wherein the lower extremity of said protuberance is located approximately three fingers above the navel.

28. The method of claim 26 or 27 wherein said device is worn for at least several hours.

29. The method of claim 28 wherein said device is worn for such duration and with such frequency as to achieve effective weight loss.

30. The method of claim 28 wherein said protuberance contains at least one hollow cavity and including the step of tapping said protuberance from time to time.

* * * * *